United States Patent
Cedergren et al.

(10) Patent No.: US 7,247,485 B1
(45) Date of Patent: Jul. 24, 2007

(54) KARL FISCHER REAGENT

(75) Inventors: Anders Cedergren, Umeå (SE); Ulrika Nordmark, Umeå (SE)

(73) Assignee: Teknikbrostiftelsen, Umea (SE)

( * ) Notice: Subject to any disclaimer, the term of this patent is extended or adjusted under 35 U.S.C. 154(b) by 0 days.

(21) Appl. No.: 09/979,313

(22) PCT Filed: May 18, 2000

(86) PCT No.: PCT/SE00/00987

§ 371 (c)(1),
(2), (4) Date: Mar. 11, 2002

(87) PCT Pub. No.: WO00/72003

PCT Pub. Date: Nov. 30, 2000

(30) Foreign Application Priority Data

May 21, 1999 (SE) .................... 9901857

(51) Int. Cl.
*G01N 33/18* (2006.01)
(52) U.S. Cl. ............... 436/42; 436/39; 436/40; 436/150; 436/151
(58) Field of Classification Search ............ 436/39–40, 436/42, 149–151
See application file for complete search history.

(56) References Cited

U.S. PATENT DOCUMENTS

| | | | |
|---|---|---|---|
| 2,967,155 A * | 1/1961 | Blomgren et al. ............ 436/42 |
| 4,354,853 A * | 10/1982 | Dahms ........................ 436/42 |
| 4,378,972 A * | 4/1983 | Scholz ......................... 436/42 |
| 4,619,900 A * | 10/1986 | Scholz ......................... 436/42 |
| 4,802,957 A | 2/1989 | Kuwata et al. |
| 4,874,709 A * | 10/1989 | Fischer et al. ................ 436/42 |
| 5,139,955 A | 8/1992 | Scholz |
| 5,401,662 A | 3/1995 | Matschiner et al. |
| 5,453,377 A | 9/1995 | Dahms |
| 5,567,618 A | 10/1996 | Scholz |
| 5,567,648 A | 10/1996 | Gupta |
| 6,361,670 B1 * | 3/2002 | Cedergren ................... 204/405 |

FOREIGN PATENT DOCUMENTS

| EP | 0 127 740 | 12/1984 |
|---|---|---|
| JP | 55-024652 | * 2/1980 |
| WO | 98/28616 | * 7/1998 |

OTHER PUBLICATIONS

Oradd, C. et al, Analytical Chemistry 1994, 66, 2603-2607.*
Cedergren, A. Analytical Chemistry 1996, 68, 784-791.*
Cedergren, A. Analytical Chemistry 1996, 68, 3682-3687.*
Cedergren, A. et al, Analytical Chemistry 1997, 69, 3100-3108.*
Cedergren, A. et al, Analytical Chemistry 1998, 70, 2174-2180.*

* cited by examiner

Primary Examiner—Arlen Soderquist

(57) ABSTRACT

Karl Fischer reagent comprising iodide, sulphur dioxide with an initial concentration above 0.5 M, and imidazole/imidazole derivative dissolved in alcoholic solvent, whereby the molar ratio between the initial imidazole/imidazole derivative concentration and the initial sulphur dioxide concentration is above 10. The reagent contains a modifying substance that is an aliphatic hydrocarbon, or a primary or secondary alcohol, or a combination thereof. A method for the determination of water content by means of Karl Fischer coulometric titration in a diaphragm-free cell, whereby the Karl Fischer reagent is used, and the coulometric titration is carried out in a diaphragm-free cell. Use of the Karl Fischer reagent in a method for the determination of water content by means of coulometric titration.

16 Claims, 1 Drawing Sheet

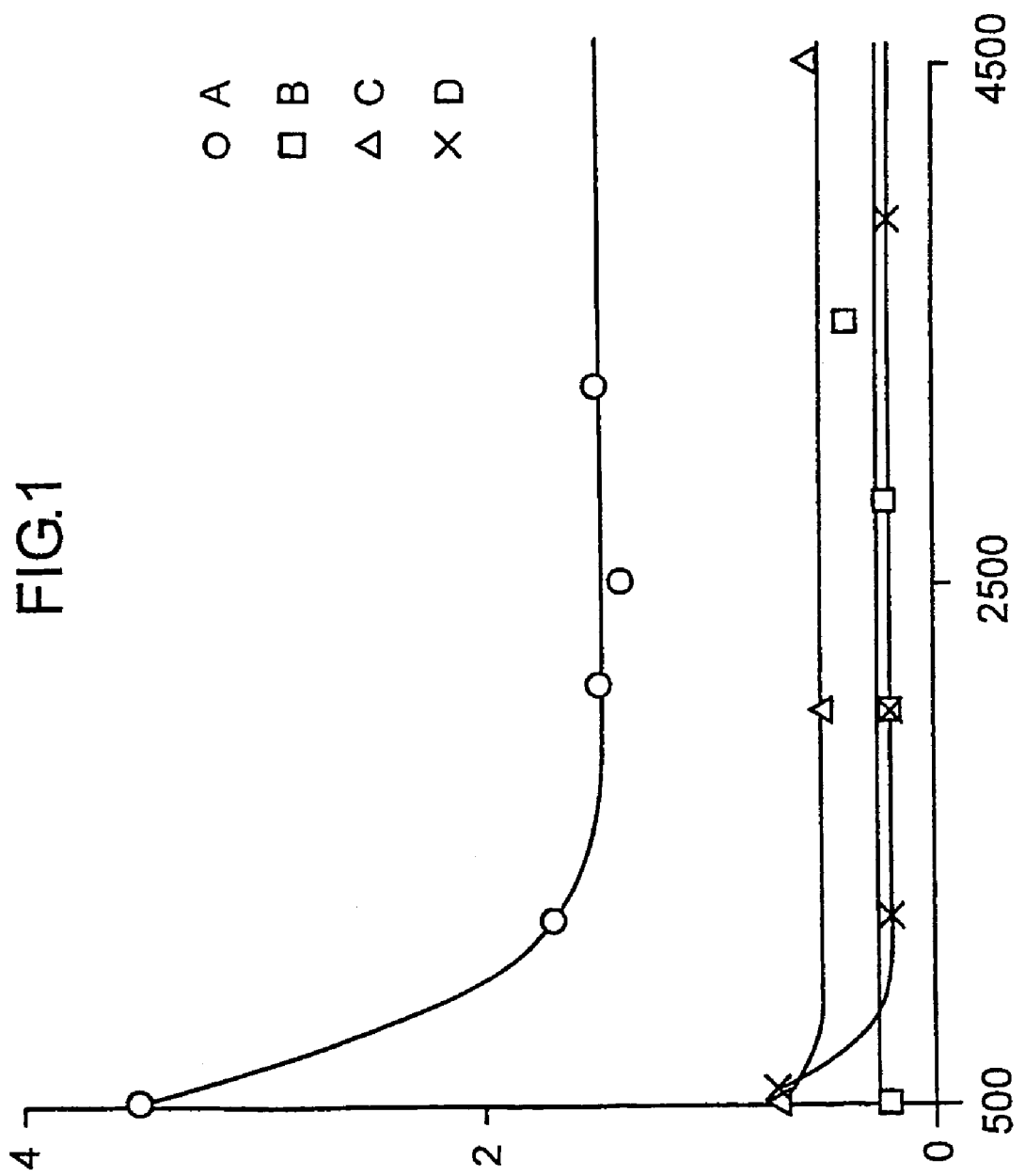

KARL FISCHER REAGENT

The present invention relates to a Karl Fischer reagent, comprising iodine, sulphur dioxide and imidazole or an imidazole derivative, all dissolved in an alcoholic solvent. In particular, it relates to the use of such a reagent in a method for the determination of water content by means of Karl Fischer coulometric titration, which is carried out in a diaphragm-free cell.

The Karl Fischer (KF) coulometric titration method is currently used extensively (500 000 determinations per day) and is considered to be of special importance for the determination of low concentrations of water. A conventional coulometric cell is equipped with a cathodic compartment, which is in electrolytic contact with the anode via a diaphragm. In this way the iodine formed in the anode reaction is hindered from reaching the cathode where it can be reduced. In addition, the diaphragm makes it possible to use a separate solution in the cathode compartment in order to eliminate the influence of the reduction products formed in the cathodic reaction. When spent KF reagent is used both as catholyte and anolyte, problems arise because sulphur dioxide/methylsulphate are reduced and the reduction products of these sulphur compounds, e.g., hydrogen sulphide, sulphide and thiosulphate, can diffuse/migrate into the anodic chamber where they are oxidised by iodine. Nowadays, it is recommended that a catholyte without sulphur dioxide, normally a soluble ammonium salt, be used. With such an electrolyte, inert hydrogen is believed to be formed quantitatively at the cathode.

Except for the need to use two different electrolytes in coulometric cells containing a diaphragm, there are additional problems associated with this concept, e.g., the relative long conditioning times needed before starting up. Clogging of the diaphragm is also known to be problematic since the resulting increase in cell resistance may cause electronic problems. These drawbacks explain the development towards the use of cells without a diaphragm that has been described in the literature during recent years, for instance in U.S. Pat. No. 5,300,207.

In principle, three different designs of such cells have been proposed i) the cathode is placed together with the anode in a single compartment; ii) the cathode is held inside a tube-like cathodic compartment having an open cylindrical hole at the bottom and the liquid inside this compartment can be drained by pushing a Teflon plunger down and up (the accumulated oxidisable reduction products are thus eliminated in a simple way); iii) the cathode is situated in a semi-open cathodic compartment which means that there will be delayed mixing of the electrolytes in contact with the anode and the cathode.

Irrespective of the type of diaphragm-free coulometric cell used, the fundamental requirement for obtaining results with high accuracy is that a negligible fraction of the generating current causes the formation of oxidisable reduction products at the cathode.

U.S. Pat. No. 5,139,955 suggests, in this regard, to use a Karl Fischer reagent comprising iodide, sulphur dioxide, and imidazole and/or imidazole derivative and/or diethanolamine and/or triethanolamine, all dissolved in an alcoholic solvent. In the examples provided in U.S. Pat. No. 5,139,955, the initial sulphur dioxide concentration varies between 0.3 and 1.0 M, and the molar ratio between the initial imidazole or imidazole derivative concentration and the initial sulphur dioxide concentration varies between 0.5 and 2.14. The technology set forth by U.S. Pat. No. 5,139,955 is said to eliminate the interference caused be the after-diffusion of oxidisable constituents from the cathode space into the anode space during Karl Fischer coulometry in a diaphragm-free cell. However, there is no indication in U.S. Pat. No. 5,139,955 that the formation of oxidisable reduction products at the cathode is actually reduced.

It has now, however, been found that this problem can be solved by means of the Karl Fischer reagent according to the present invention, as defined by the appended claims.

More particularly, the Karl Fischer reagent according to the present invention comprises iodide, sulphur dioxide, and imidazole and/or an imidazole derivative, all dissolved in an alcoholic solvent, whereby the initial sulphur dioxide concentration is above 0.5 M, preferably from about 0.55 M, and in particular from about 0.6 M; the molar ratio between the initial imidazole or imidazole derivative concentration and the initial sulphur dioxide concentration is above 10, preferably from about 10.5, and in particular from about 11; and that the reagent contains a modifying substance that is an aliphatic hydrocarbon, or a primary or secondary alcohol, or a combination thereof.

In the present application the expression "initial . . . " signifies values relating to a component or components before having reacted with any other component and in particular before having reached equilibrium in such a reaction.

In a preferred embodiment, the modifier is an aliphatic chlorinated hydrocarbon, in particular a $C_1$-$C_7$ hydrocarbon, such as chloroform, carbon tetrachloride, methylene chloride, or a combination of such hydrocarbons.

In another preferred embodiment, the modifier is a $C_3$-$C_{10}$ alcohol, such as butanol, pentanol, hexanol, or a combination of such alcohols.

Examples of imidazole derivatives used according to the invention are 1-methylimidazole, 1-ethylimidazole, 1-propylimidazole, 1-butylimidazole, 2-methylimidazole, 2-ethylimidazole, 2-propylimidazole, 2-butylimidazole, 4-methylimidazole, 4-butylimidazole, 1,2-dimethylimidazole, 1,2,4-trimethylimidazole, 1-phenylimidazole, 2-phenylimidazole and benzimidazole. The initial concentration of imidazole and/or imidazole derivatives is preferably in the range of 5-8 M.

The Karl Fischer reagent according to the present invention also comprises sulphur dioxide in an initial concentration of above 0.5, preferably in the range 0.5-0.8 M. The reagent according to the invention comprises, in addition, at least one soluble iodide which can be anodically oxidised to iodine and thus ensures that the Karl Fischer reaction proceeds. Alkali iodides or alkaline earth iodides such as, for example, sodium iodide, potassium iodide, lithium iodide, calcium iodide, can be used as soluble iodides. Hydroiodides of organic bases, for example of trimethylamine or triethylamine, are also suitable. Preferably used are the hydroiodides of the reactive bases that are used in the reagent according to the invention, that is to say, for example, imidazole hydroiodide, 1-alkylimidazole hydroiodide, 2-alkylimidazole hydroiodide, and diethanolamine hydroiodide or triethanolamine hydroiodide. The reagent according to the invention contains an iodide or a mixture of different iodides. The iodide concentration in the reagent according to the invention is between 0.05 M and 1 M. In the preparation of the reagent, the iodides may be added directly as salts or, alternatively, be prepared by reacting iodine with water in the finally formulated reagent. The reactivity of reagent can be decreased by increasing iodide concentration, which is of particular importance for the object of minimising side reactions between the reagent and any iodine consuming substances in a sample.

For the purpose of the present invention, an alcoholic solvent is understood to be a monohydric or dihydric alcohol that contains 1 to 3 carbon atoms and which may be substituted with 1 to 4 halogen atoms. Possible halogen atoms for the substituents of the alcohol are bromine, iodine, fluorine and preferably chlorine atoms. Examples of suitable alcohols are: methanol, ethanol, propanol, ethylene glycol, propylene glycol, 1,3-propanediol, 2-methoxyethanol, 2-chloroethanol, 2-bormoethanol, 2-iodoethanol, 2-fluoroethanol, 2,2,2-trifluoroethanol, 1-bromo-2-propanol, 2-chloro-1-propanol, 3-chloro-1,2-propanediol, 2,2,3,3-tetrafluoro-1-propanol, benzyl alcohol, 2-bromobenzyl alcohol, 3-methoxybenzyl alcohol, 4-methoxybenzyl alcohol, 4-methylbenzyl alcohol, 1-phenylethanol, 2-phenylethanol, 2-phenoxyethanol, benzhydrol and tetraphenylethanediol. The alcohols are used individually or, alternatively, mixed with one another. Optionally they are employed mixed with one or more other additional organic solvents, the amount of the alcohol being more than 10, preferably at least 25 percent by weight of the solvent mixture.

Additional bases may be used in the present reagent, in particular for the purpose of adjusting the pH. Exemplary of suitable bases is sodium acetate and various amines such as diethanolamine, triethanolamine, and morpholine. These bases may be contained individually or as a mixture.

Furthermore, the reagents according to the invention may contain one or more additional conducting salts to improve its conductance. The anions of these conducting salts may be derived from inorganic acids such as, for example, hydrogen halides, sulphuric acid, sulphurous acid, or from organic acids such as, for example benzoic acid and salicylic acid. The cations of the conducting salts may also be of an inorganic or organic nature. Inorganic cations are, for example, cations of alkali metals, in particular of lithium, sodium, potassium, caesium and the alkaline earth metals, in particular of calcium and barium. Halides such as sodium bromide, sodium iodide, potassium bromide, potassium iodide, caesium chloride, tetrabutyl bromide, calcium iodide, barium bromide, lithium benzoate or sodium salicylate are suitable. Preferably used are salts whose cations or anions are contained in the reagent according to the invention, for example imidazole hydrobromide, 1-methylimidazole hydrochloride, diethanolamine hydrochloride, diethanolammonium benzoate, imidazolinium salicylate, triethanolammonium methyl sulphite, imidazolinium methyl sulphite. Salts of the alkyl esters of sulphurous acid that are formed from sulphur dioxide and the alcohols used are also suitable as the iodides of the reactive bases used. Reaction products of the Karl Fischer reaction such as, for example, the alkyl sulphates of the bases contained, can also be used as conducting salts. The conducting salts may be added to the reagent during the preparation, but may also be produced during the preparation by reacting the co-reactants, for example the alkyl sulphates by reacting alcohol, sulphur dioxide and the corresponding base or the alkyl sulphates by oxidising the alkyl sulphites by means of iodine in the presence of water.

The present invention also relates to a method for the determination of water content by means of Karl Fischer coulometric titration in a diaphragm-free cell, whereby a Karl Fischer reagent, comprising an iodide, sulphur dioxide and imidazole or an imidazole derivative, all dissolved in an alcoholic solvent, is used, and the coulometric titration is carried out in a diaphragm-free cell, whereby the Karl Fischer reagent is a reagent in which the initial sulphur dioxide concentration is above 0.5 M, preferably from about 0.55 M, and in particular from about 0.6 M; the molar ratio between the initial imidazole or imidazole derivative concentration and the initial sulphur dioxide concentration is above 10, preferably from about 10.5, and in particular from about 11; and the reagent contains a modifying substance that is an aliphatic hydrocarbon, or a primary or secondary alcohol, or a combination thereof.

In a preferred embodiment of the inventive method the Karl Fischer reagent is buffered at about pH 10. Preferably, the cathodic current density is in the range of about 500-5000 $mA/cm^2$. The coulometric titration of the inventive method may be based on continuous electrolysis, but may as well be based on pulsed electrolysis.

The present invention also relates to the use of a Karl Fischer reagent as described above in a method for the determination of water content by means of coulometric titration.

Below, the present invention will be further illustrated by means of example. The general conditions for experiments underlying those examples are as follows:

Chemicals

Chloroform (pa) and carbon tetrachloride (pa) were from Merck. Imidazole (pa) and sulphur dioxide (>99.9%) were from Fluka. Iodine (pa), hexanol (99%), acetic acid (pa), and sodium acetate (pa) were from Riedel-deHaën. Methanol (pa) was from KeboLab. Salicylic acid was from Analar (99.9%).

Reagents pH measurements were made using a Metrohm pH meter with saturated lithium chloride in methanol as internal electrolyte. Buffer solutions (0.05 M) were prepared in methanol from salicylic acid/sodium salicylate (pH 7.9) and acetic acid/sodium acetate (pH 9.7). The effective sulphur dioxide concentration $[SO_2]_{eff}$ (i.e. the sum of all S(IV) species obtained from the added sulphur dioxide) was determined coulometrically according to the method described by Cedergren et al. in Anal. Chem. 1978, 47, 100-106.

Instrumentation

Two different cells were used for coulometric KF-titrations, a three compartment cell and a diaphragm-free cell. The former consisted of three chambers, the reference electrode (Pt) in the left chamber, the working (Pt) and the indicating electrode (Pt) where the sample is injected through a silicone rubber septum in the middle and finally the right chamber for the auxiliary electrode (Pt). A plug containing a small channel was placed in the chamber where the reduction takes place. One additional platinum wire electrode was placed in the middle chamber near the working electrode and was used as a cathode in the investigation of the formation of oxidizable reduction products. This electrode was coated with a thin layer of fluorinated ethylene propylene (FEP) except for a surface area of 0.002 $cm^2$. The maximum current that can be used in the generating electrode system, when using this small cathode surface, was about 10 mA for a 10 V output voltage from the titrator. For the normally used 28 V, the maximum current should be 28 mA, which corresponds to a maximum titration rate of 156.8 μg water per minute. No cleaning of electrodes was necessary under normal operating conditions. Asbestos-filled liquid junctions made electrolytic contact between the chambers. The diaphragm-free cell was equipped with a platinum cathode (0.002 $cm^2$) inside a tube-like cathodic compartment with a draining function. By pushing down a Teflon plunger this cathode could be brought in direct contact with the anolyte. Samples were injected through a silicone rubber septum. Both cells were connected to the computer controlled coulometric titrator (zero-current potentiometric endpoint indication) described in Anal. Chem. 1998, 70, 5332-5338.

Procedure

Procedures for preparation of the three-compartment cell (5 ml) and the diaphragm-free cell (13 ml) have been described in detail in Anal. Chem. 1998, 70, 2174-80 and Anal. Chem. 1997, 69, 3100-8, respectively. For calibration, i.e. the establishment of the relation between the redox potential of the indicating electrode and the excess iodine, the same procedure as that outlined in Anal. Chem. 1998, 70, 5332-38 was used.

Calculations

The base-line drift (corresponding to the moisture diffusing into the coulometric cell) was typically in the range 0.1-1.0 µg $H_2O$/min and this value was obtained with the cathode placed in the cathodic compartment of the respective cell. The difference between this value and that obtained when the cathode was operated in direct contact with the anolyte i.e. at the background level, was used in the calculations of the extent of formation of oxidizable reduction products at a certain current. This was done by multiplying this drift difference with the time for the titration and the product was then added to the integrated value (corrected for the background), and compared to that obtained for the standard (obtained with the cathode in the cathodic compartment). Irrespective of what type of reagent was used the values obtained for this standard (50 µg water) did not vary by more than 0.5% (relative) during a 9 months period.

Examples

The influence of carbon tetrachloride, chloroform and hexanol was investigated for an imidazole-buffered reagent having an initial imidazole concentration of 6.6 M, an initial sulphur dioxide concentration of 0.6 M, and an initial iodine concentration of 0.1 M.

Carbon tetrachloride, chloroform, and hexanol were added to this reagent according to the table below. The pH of all reagents was 10.

| Reagent | Carbon tetrachloride initial concentration (M) | Chloroform initial concentration (M) | Hexanol initial concentration (M) |
| --- | --- | --- | --- |
| A | 0 | 0 | 0 |
| B | 1 | 0 | 0 |
| C | 0 | 1 | 0 |
| D | 0 | 0 | 1 |

These reagents were investigated regarding formation of oxidisable reduction products in relation to applied current density, and the results, for 50 µg samples, are given in FIG. 1. In the graph in FIG. 1, the relative percentage error is set of on the ordinate against applied current density (in mA/cm$^2$) indicated on the abscissa.

By comparison with the result obtained without modifier (reagent A), it can be seen that there is a significant decrease in the formation of oxidizable reduction products when any of these modifiers is present.

For all modified reagents at pH 10 a very favourable situation prevails, since the relative formation is well below 1% over a large range of current densities. It can be concluded that for very low current densities, carbon tetrachloride is the most effective modifier while hexanol is more efficient at higher current densities.

The invention claimed is:

1. A method for the determination of water content by means of Karl Fischer coulometric titration in a diaphragm-fee cell, whereby a Karl Fischer reagent, consisting essentially of iodide, sulphur dioxide, imidazole or an imidazole derivative, and a modifying substance for decreased production of oxidisable reduction products compared to a similar Karl Fischer reagent without said modifying agent, all dissolved in an alcoholic solvent, is used, and the coulometric titration is carried out in a diaphragm-free cell, characterized in that said Karl Fischer coulometric titration reagent is a reagent in which the initial sulphur dioxide concentration is above 0.5 M, the molar ratio between the initial imidazole or imidazole derivative concentration and the initial sulfur dioxide concentration is 10.5 or above, wherein the modifying substance is hexanol.

2. A method according to claim 1, characterized in that the Karl Fisher reagent is buffered at about pH 10.

3. A method according to claim 1, characterized in that the cathodic current density is in the range of about 500-5000 mA/cm$^2$.

4. A method according to claim 1 wherein the initial sulphur dioxide concentration is about 0.55M.

5. A method according to claim 1 wherein the initial sulphur dioxide concentration is about 0.6M.

6. A method according to claim 1 wherein the molar ratio between the initial imidazole or imidazole derivative and the initial sulfur dioxide concentration is 10.5.

7. A method according to claim 1 wherein the molar ratio between the initial imidazole or imidazole derivative and the initial sulfur dioxide concentration is 11.

8. A method according to claim 1 wherein the initial sulphur dioxide concentration is about 0.6M and the molar ratio between the initial imidazole or imidazole derivative and the initial sulfur dioxide concentration is 11.

9. A method according to claim 1 wherein the alcoholic solvent is selected from monohydric or dihydric alcohol that contains 1 to 3 carbon atoms and may be substituted with 1 to 4 halogen atoms, and mixtures thereof.

10. A Karl Fischer coulometric titration reagent, consisting essentially of iodide, sulphur dioxide, imidazole or an imidazole derivative, and a modifying substance for decreased production of oxidisable reduction products compared to a similar Karl Fischer reagent without said modifying agent, all dissolved in an alcoholic solvent, characterized in that the initial sulphur dioxide concentration is above 0.5 M, the molar ratio between the initial imidazole or imidazole derivative concentration and the initial sulfur dioxide concentration is 10.5 or above 40, wherein the modifying substance is hexanol.

11. A Karl Fischer coulometric titration reagent according to claim 10 wherein the initial sulphur dioxide concentration is about 0.55M.

12. A Karl Fischer coulometric titration reagent according to claim 10 wherein the initial sulphur dioxide concentration is about 0.6M.

13. A Karl Fischer coulometric titration reagent according to claim 10 wherein the molar ratio between the initial imidazole or imidazole derivative and the initial sulfur dioxide concentration is 10.5.

14. A Karl Fischer coulometric titration reagent according to claim 10 wherein the molar ratio between the initial imidazole or imidazole derivative and the initial sulfur dioxide concentration is 11.

15. A Karl Fischer coulometric titration reagent according to claim 10 wherein the initial sulphur dioxide concentration is about 0.6M and the molar ratio between the initial imidazole or imidazole derivative and the initial sulfur dioxide concentration is 11.

16. A Karl Fischer coulometric titration reagent according to claim 10 wherein the alcoholic solvent is selected from monohydric or dihydric alcohol that contains 1 to 3 carbon atoms and may be substituted with 1 to 4 halogen atoms, and mixtures thereof.

* * * * *